(12) United States Patent
Markworth

(10) Patent No.: US 7,695,500 B2
(45) Date of Patent: Apr. 13, 2010

(54) POLYAXIAL OCCIPITAL PLATE

(75) Inventor: Aaron D. Markworth, Saddle Brook, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 327 days.

(21) Appl. No.: 11/750,503

(22) Filed: May 18, 2007

(65) Prior Publication Data
US 2007/0233119 A1  Oct. 4, 2007

Related U.S. Application Data

(63) Continuation-in-part of application No. 11/567,380, filed on Dec. 6, 2006, which is a continuation-in-part of application No. 11/373,386, filed on Mar. 10, 2006.

(51) Int. Cl.
*A61B 17/70* (2006.01)
(52) U.S. Cl. .............. 606/280; 606/246; 606/250; 606/70; 606/71
(58) Field of Classification Search ............. 606/70–71, 606/246, 247, 250–253, 280–299; 403/64, 403/169–170, 174, 178
See application file for complete search history.

(56) References Cited

U.S. PATENT DOCUMENTS

| | | | |
|---|---|---|---|
| 5,507,745 A | 4/1996 | Logroscino et al. | |
| 5,542,946 A | 8/1996 | Logroscino et al. | |
| 5,558,674 A | 9/1996 | Heggeness et al. | |
| 6,146,382 A | 11/2000 | Hurlbert | |
| 6,217,578 B1 | 4/2001 | Crozet et al. | |
| 6,299,614 B1 | 10/2001 | Kretschmer et al. | |
| 6,302,822 B1 | 10/2001 | Suzuki et al. | |
| 6,432,108 B1 | 8/2002 | Burgess et al. | |
| 6,524,310 B1 | 2/2003 | Lombardo et al. | |
| 6,524,315 B1 | 2/2003 | Selvitelli et al. | |
| 6,547,790 B2 | 4/2003 | Harkey, III et al. | |
| 6,709,435 B2 * | 3/2004 | Lin ............................ | 606/250 |
| 6,736,817 B2 | 5/2004 | Trozell et al. | |
| 6,761,721 B2 | 7/2004 | Burgess et al. | |
| 6,793,657 B2 | 9/2004 | Lee et al. | |
| 6,875,211 B2 | 4/2005 | Nichols et al. | |
| 6,902,565 B2 | 6/2005 | Berger et al. | |
| 2003/0187435 A1 * | 10/2003 | Lin .............................. | 606/61 |
| 2004/0106924 A1 * | 6/2004 | Ralph et al. ................... | 606/71 |
| 2005/0240181 A1 * | 10/2005 | Boomer et al. ................ | 606/61 |
| 2007/0049932 A1 * | 3/2007 | Richelsoph et al. ........... | 606/61 |
| 2007/0118121 A1 * | 5/2007 | Purcell et al. ................. | 606/61 |
| 2008/0147123 A1 * | 6/2008 | Schermerhorn ............. | 606/278 |

\* cited by examiner

*Primary Examiner*—Eduardo C Robert
*Assistant Examiner*—Steven J Cotroneo
(74) *Attorney, Agent, or Firm*—Rahman LLC

(57) ABSTRACT

A polyaxial occipital plate assembly and method comprises a longitudinal member; a polyaxial connector head; a socket portion adapted to retain the connector head; a flexible clip operatively connected to the socket portion and adapted to receive the longitudinal member; an occipital plate comprising clips operatively connected to the connector head; and a locking mechanism operatively connected to the connector head and the clips, wherein engagement of the locking mechanism to the connector head causes the clips to lock into the connector head and outwardly expand the connector head thereby causing the flexible clip to squeeze against the longitudinal member. The plate comprises a pair of opposed legs comprising the clips attached to ends of the legs; a body portion operatively connected to the pair of opposed legs, wherein the body portion is positioned at any of an obtuse and an acute angle relative to the pair of opposed legs.

20 Claims, 9 Drawing Sheets

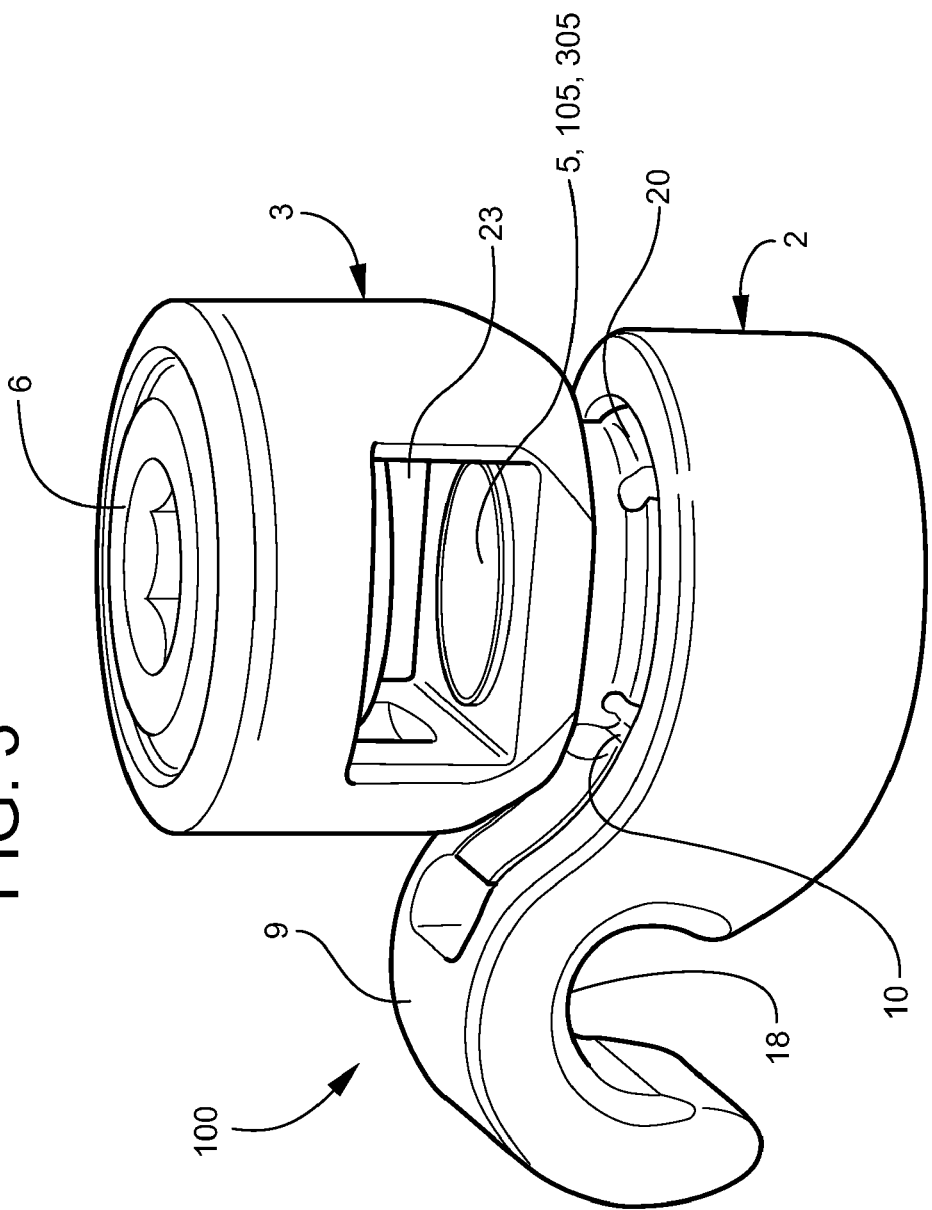

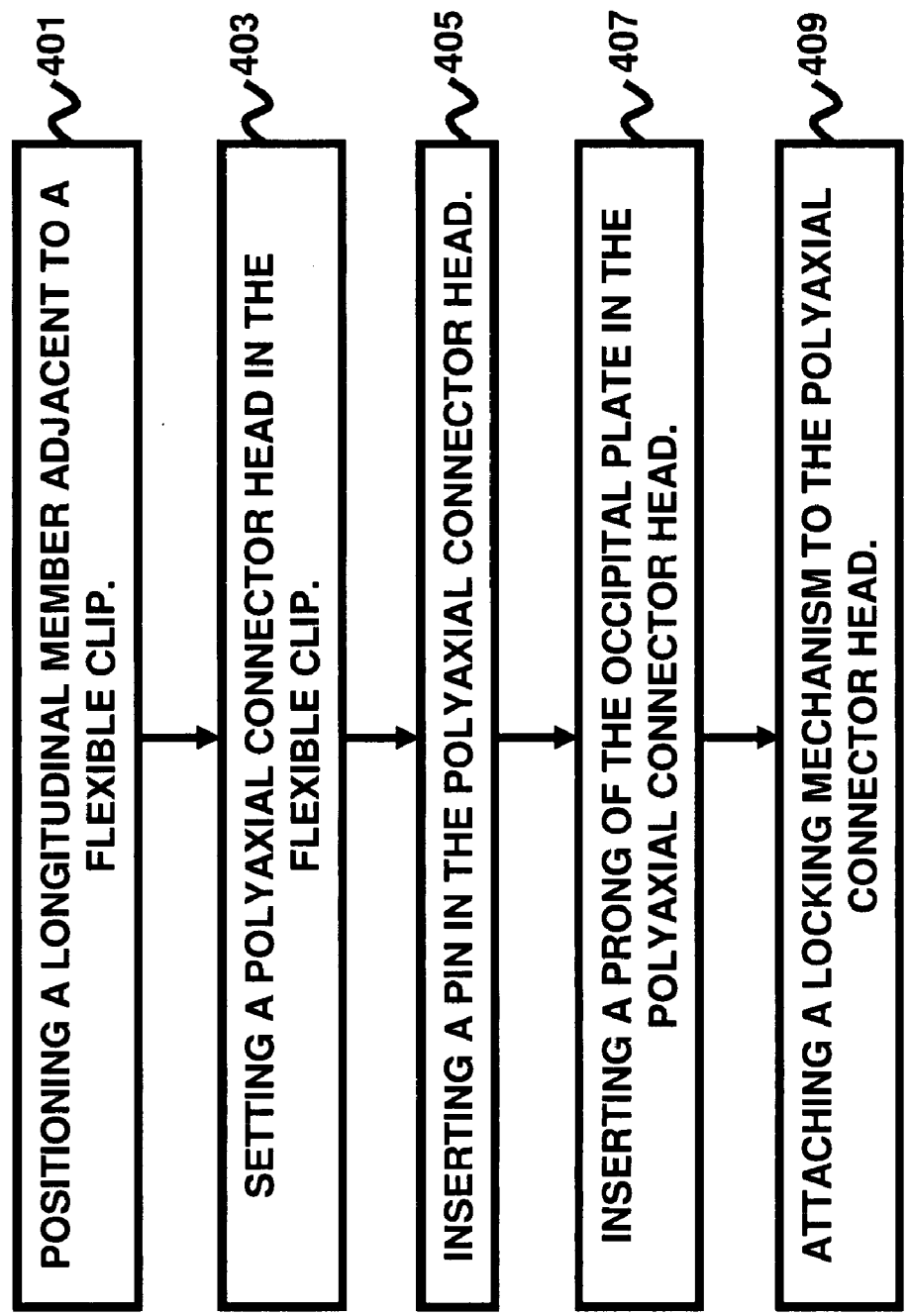

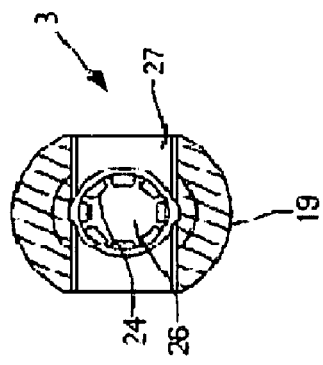
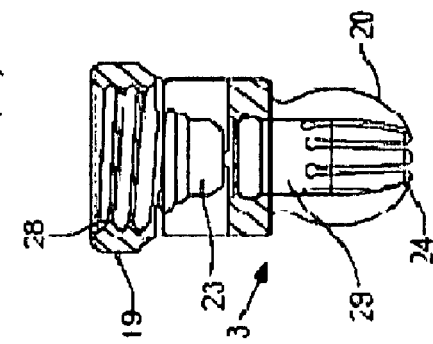
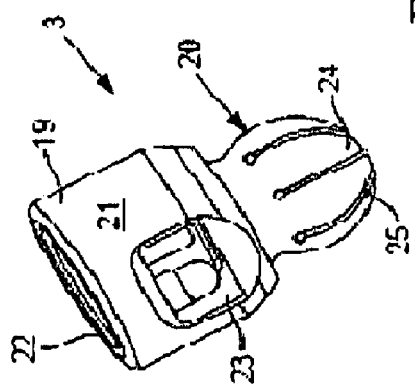
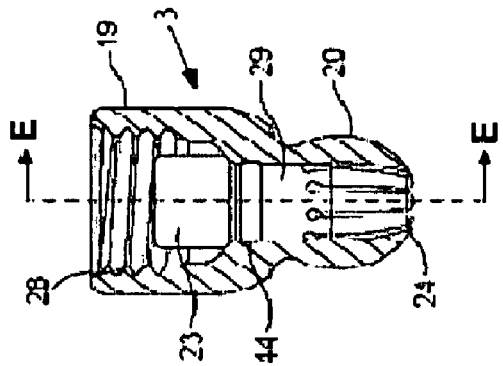
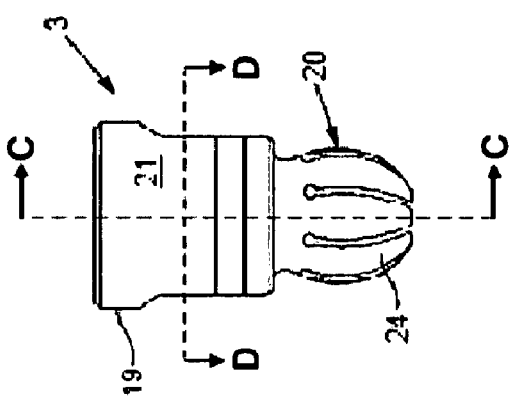

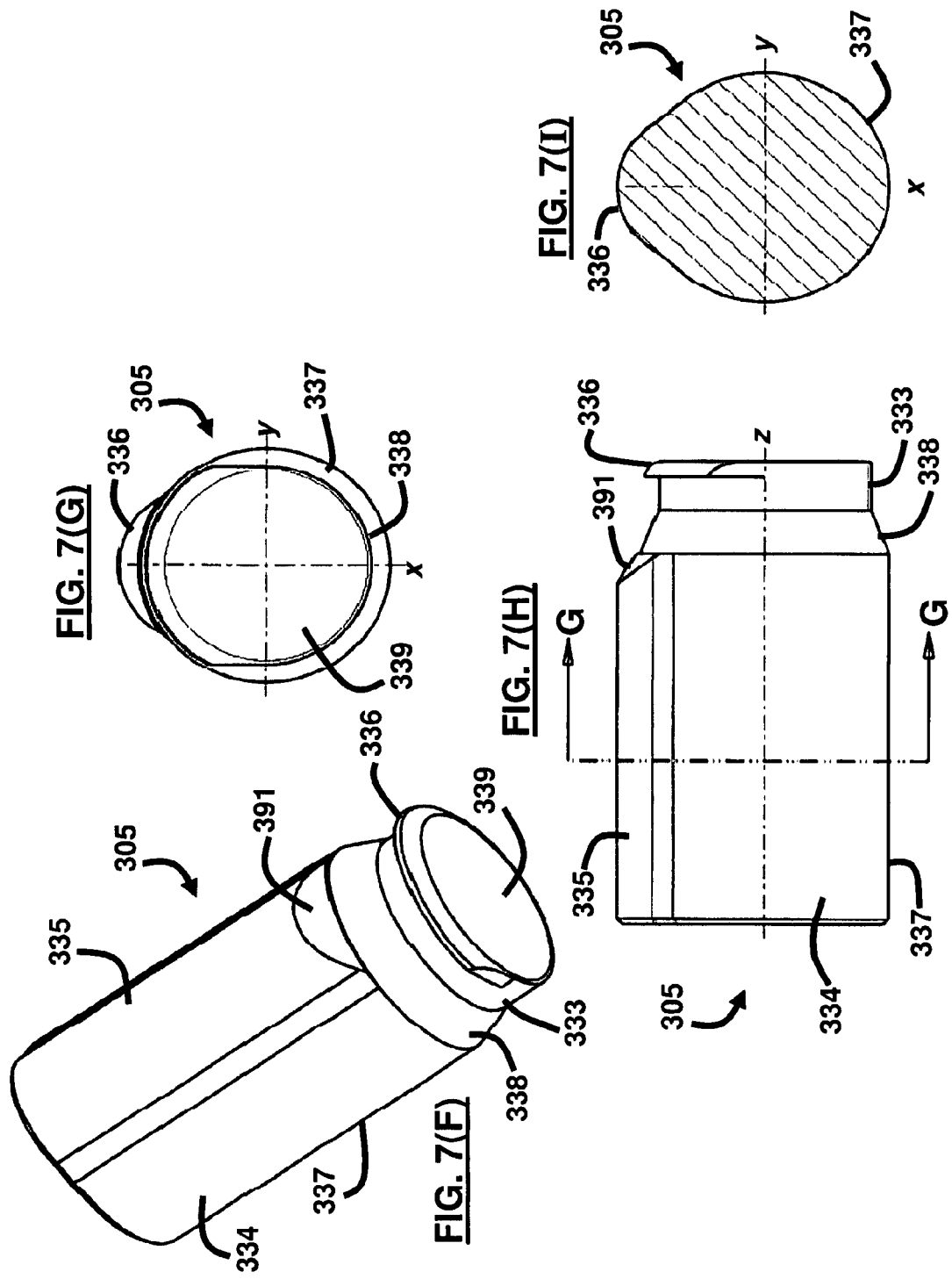

POLYAXIAL OCCIPITAL PLATE

CROSS-REFERENCE TO RELATED APPLICATIONS

This application is a continuation-in-part (CIP) of U.S. patent Ser. No. 11/567,380, filed on Dec. 6, 2006 and entitled "Spinal Cross-Connector," (hereinafter "the '380 cross-connector") and assigned to Custom Spine, Inc. of Parsippany, N.J., which is a CIP of U.S. patent Ser. No. 11/373,386, filed on Mar. 10, 2006 and entitled "Spinal Cross-Connector," (hereinafter "the '386 cross-connector") and assigned to Custom Spine, Inc. of Parsippany, N.J., the complete disclosures of which, in their entireties, are herein incorporated by reference.

BACKGROUND

1. Technical Field

The embodiments herein generally relate to medical devices, and, more particularly, to occipital plate implant assemblies.

2. Description of the Related Art

There are many occipital plate implants on the market today. Some implants have through-holes and must be pre-loaded on the rod. Others have top loading sockets similar to polyaxial screws which allow bent rods to be anchored to the plate. The most simple, but generally most difficult, to use form is that of a rod that smoothly tapers to an occipital plate that must be bent and contoured to match highly varied anatomy. All of these iterations have at most one to two degrees of freedom and typically require long preparation time to ensure a proper bend. This makes the implants both difficult to connect to the longitudinal rod member and the occipital plateau without putting stress on the atlantoaxial joint. Accordingly, there remains a need for a new medical device that is a capable of connecting to the longitudinal members of a cervico-thoracic spinal fusion construct to an occipital plate providing improved ease of use.

SUMMARY

In view of the foregoing, an embodiment provides a polyaxial occipital plate assembly comprising a longitudinal member; a polyaxial connector head; a socket portion adapted to retain the polyaxial connector head; a flexible clip operatively connected to the socket portion and adapted to receive the longitudinal member; an occipital plate comprising clips operatively connected to the polyaxial connector head; and a locking mechanism operatively connected to the polyaxial connector head and the clips, wherein engagement of the locking mechanism to the polyaxial connector head causes the clips to lock into the polyaxial connector head and outwardly expand the polyaxial connector head thereby causing the flexible clip to squeeze against the longitudinal member. The occipital plate may further comprise a pair of opposed legs comprising the clips attached to ends of the legs; a body portion operatively connected to the pair of opposed legs, wherein the body portion is positioned at any of an obtuse angle and an acute angle relative to the pair of opposed legs. Moreover, the flexible clip preferably comprises a flexible bias member adapted to retain the longitudinal member.

Preferably, the locking mechanism comprises a pin portion operatively connected to the connector body and the polyaxial connector head; and a blocker mechanism operatively connected to the clips and the polyaxial connector head, wherein the pin portion is adapted to engage the flexible bias member causing the longitudinal member to become affixed to the flexible clip. Furthermore, the polyaxial connector head may comprise an upper portion comprising a first hole adapted to engage the locking mechanism; and a second hole adapted to accommodate the clips of the occipital plate, wherein the first hole and the second hole are transversely positioned with respect to one another. Additionally, the polyaxial connector head preferably comprises a bulbous end connected to the upper portion and adapted to sit in the socket portion of the connector body, wherein the bulbous end comprises a plurality of flexible prongs separated from one another by slots; and an opening extending through the bulbous end and extending to the first hole. Also, the locking mechanism may be adapted to engage the plurality of flexible prongs causing the plurality of flexible prongs to outwardly bend and lock the polyaxial connector head to the connector body. Preferably, each of the clips of the occipital plate are bendable.

Another embodiment provides an occipital plate assembly comprising a connector body; a connector head adapted to engage the connector body; a pin operatively connected to the connector body and the connector head; an occipital plate operatively connected to the connector head and the pin; a blocker operatively connected to the connector head and the occipital plate; and a longitudinal member locked to the connector body. Preferably, the connector body comprises a flexible bias member adapted to retain the longitudinal member. Also, the connector body preferably comprises a socket portion; and a clip portion attached to the socket portion, the clip portion being adapted to retain the longitudinal member, wherein the flexible bias member extends from the clip portion to a bottom region of the portion. Additionally, the pin is preferably adapted to engage the flexible bias member causing the longitudinal member to become locked to the connector body.

Furthermore, the connector head may comprise an upper portion comprising a first opening adapted to engage the locking mechanism; and a second opening adapted to accommodate the occipital plate, wherein the first opening and the second opening are transversely positioned with respect to one another. Moreover, the connector head may comprise a bulbous end comprising a plurality of flexible prongs separated from one another by slots; and a hole extending through the bulbous end and extending to the first opening. Preferably, the pin is adapted to engage the plurality of flexible prongs causing the plurality of flexible prongs to outwardly bend and lock the bulbous end of the connector head to the flexible clip. Also, the occipital plate preferably comprises a body potion; a first leg extending from the body portion; and a second leg extending from the body portion, wherein the first and second legs are substantially parallel to one another, wherein the first and second legs each comprise slotted caudal ends that are adapted to fit through the connector head, and wherein engagement of the blocker to the connector head causes the slotted caudal ends to push the pin thereby causing outward expansion of the connector head thereby causing the flexible bias member to lock the longitudinal member to the connector body.

Another embodiment provides a method of locking a longitudinal member to a multi-pronged occipital plate, wherein the method comprises positioning a longitudinal member adjacent to a flexible clip; setting a polyaxial connector head in the flexible clip; inserting a pin in the polyaxial connector head, wherein the pin contacts the flexible clip; inserting a prong of the occipital plate in the polyaxial connector head; and attaching a locking mechanism to the polyaxial connector head, wherein the locking mechanism is operatively connected to the pin. Preferably, attachment of the locking mechanism to the polyaxial connector head causes the prong of the occipital plate to engage the pin thereby engaging the flexible clip thereby causing the flexible clip to lock the longitudinal member into a locked position. Additionally, in the positioning process, the flexible clip preferably comprises a flexible bias member, and wherein the flexible-bias member is adapted to lock the longitudinal member into a locked position. Furthermore, in the setting process, the polyaxial connector head may comprise an upper portion connected to a bulbous end, wherein the upper portion comprises a first hole adapted to engage the locking mechanism; and a second hole adapted to accommodate the occipital plate, wherein the first hole and the second hole are transversely positioned with respect to one another, wherein the bulbous end comprises a plurality of flexible prongs separated from one another by slots; and an opening extending through the bulbous end and extending to the first hole, wherein the pin is adapted to engage the plurality of flexible prongs causing the plurality of flexible prongs to outwardly bend and lock the polyaxial connector head to the flexible clip.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 3 illustrates a schematic diagram of a polyaxial cross-connector according to an embodiment herein;

FIG. 4 is a flow diagram illustrating a preferred method according to an embodiment herein;

FIG. 6(A) illustrates a perspective view of the connector head of the spinal cross-connector assembly construct of FIG. 3 according to an embodiment herein;

FIG. 6(B) illustrates a cross-sectional top view of the connector head of FIG. 6(A) cut along line D-D of FIG. 6(C) according to an embodiment herein;

FIG. 6(C) illustrates a side view of the connector head of FIG. 6(A) according to an embodiment herein;

FIG. 6(D) illustrates a cross-sectional front view of the connector head of FIG. 6(A) cut along line C-C of FIG. 6(C) according to an embodiment herein;

FIG. 6(E) illustrates a cross-sectional side view of the connector head of FIG. 6(A) cut along line E-E of FIG. 6(D) according to an embodiment herein;

FIG. 7(F) illustrates a perspective view of the locking pin of the spinal cross-connector assembly construct of FIG. 3 according to a second alternate embodiment herein;

FIG. 7(G) illustrates a bottom view of the locking pin of FIG. 7(F) according to a second alternate embodiment herein;

FIG. 7(H) illustrates a front view of the locking pin of FIG. 7(F) according to a second alternate embodiment herein;

FIG. 7(I) illustrates a cross-sectional side view of the locking pin of FIG. 7(H) cut along line G-G of FIG. 7(H) according to a second alternate embodiment herein;

DETAILED DESCRIPTION OF PREFERRED EMBODIMENTS

Figure 1:
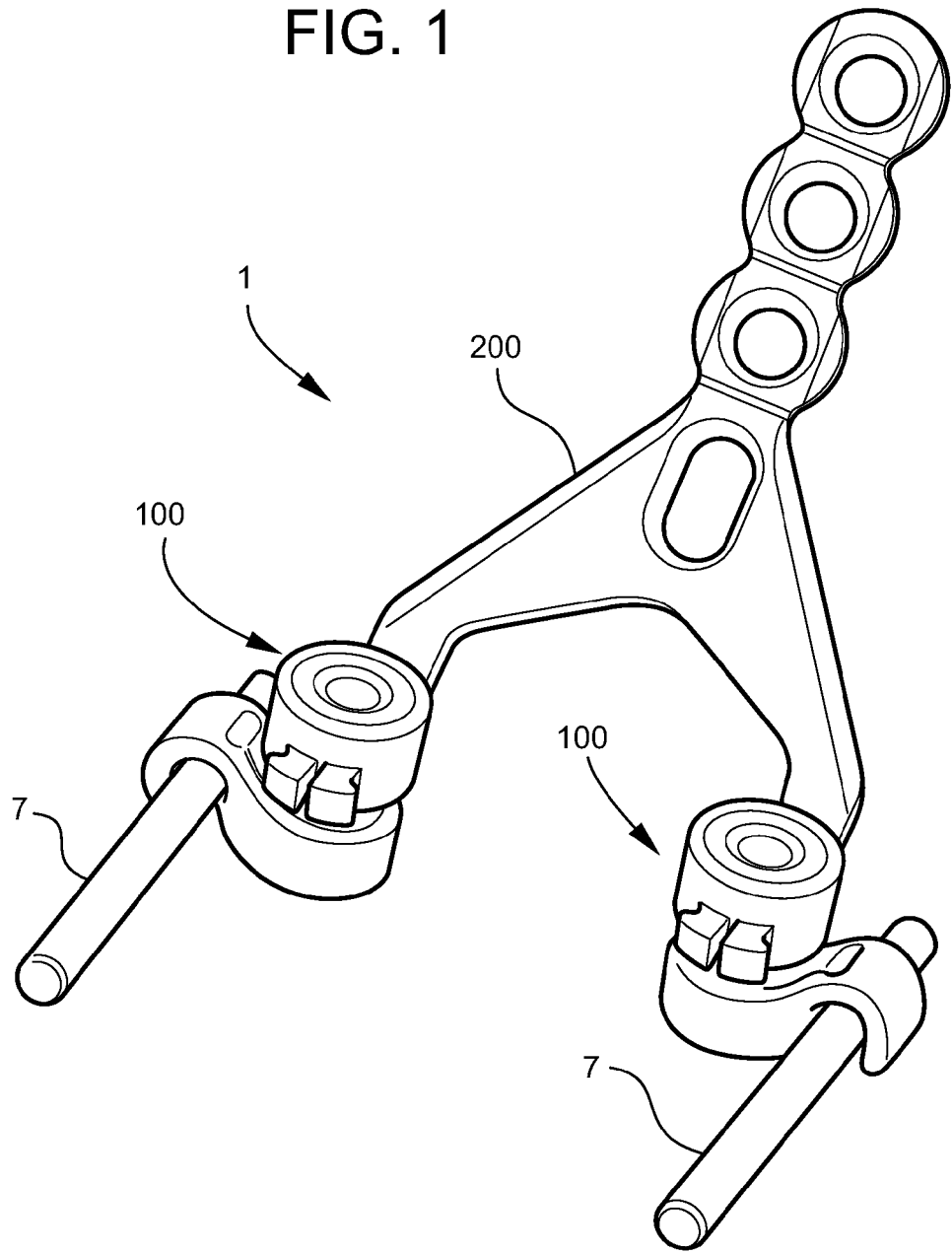
FIG. 1 illustrates a schematic diagram of an occipital plate connector assembly according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new medical device that is a capable of connecting to the longitudinal members of a cervico-thoracic spinal fusion construct to an occipital plate providing improved ease of use. The embodiments herein achieve this by providing an easy to use polyaxial connector that bridges an occipital plate component to the longitudinal rod of a spinal construct. Referring now to the drawings, and more particularly to FIGS. 1 through 8(D), where similar reference characters denote corresponding features consistently throughout the figures, there are shown preferred embodiments.

As shown in FIG. 1, the embodiments herein provide an assembly 1 comprising a pair of polyaxial cross-connectors 100 that each bridge an occipital plate 200 to a longitudinal rod 7 of a spinal construct (screw or hook) (not shown). The connector 100 is the same as the spinal cross-connector of the '386 cross-connector or the '380 cross-connector, incorporated herein by reference. The connector 100 allows extension of a cervico-thoracic construct to the occipital plateau for bilateral or sub-inion midline fixation depending on the shape of the occipital plate component 200.

Figure 2:
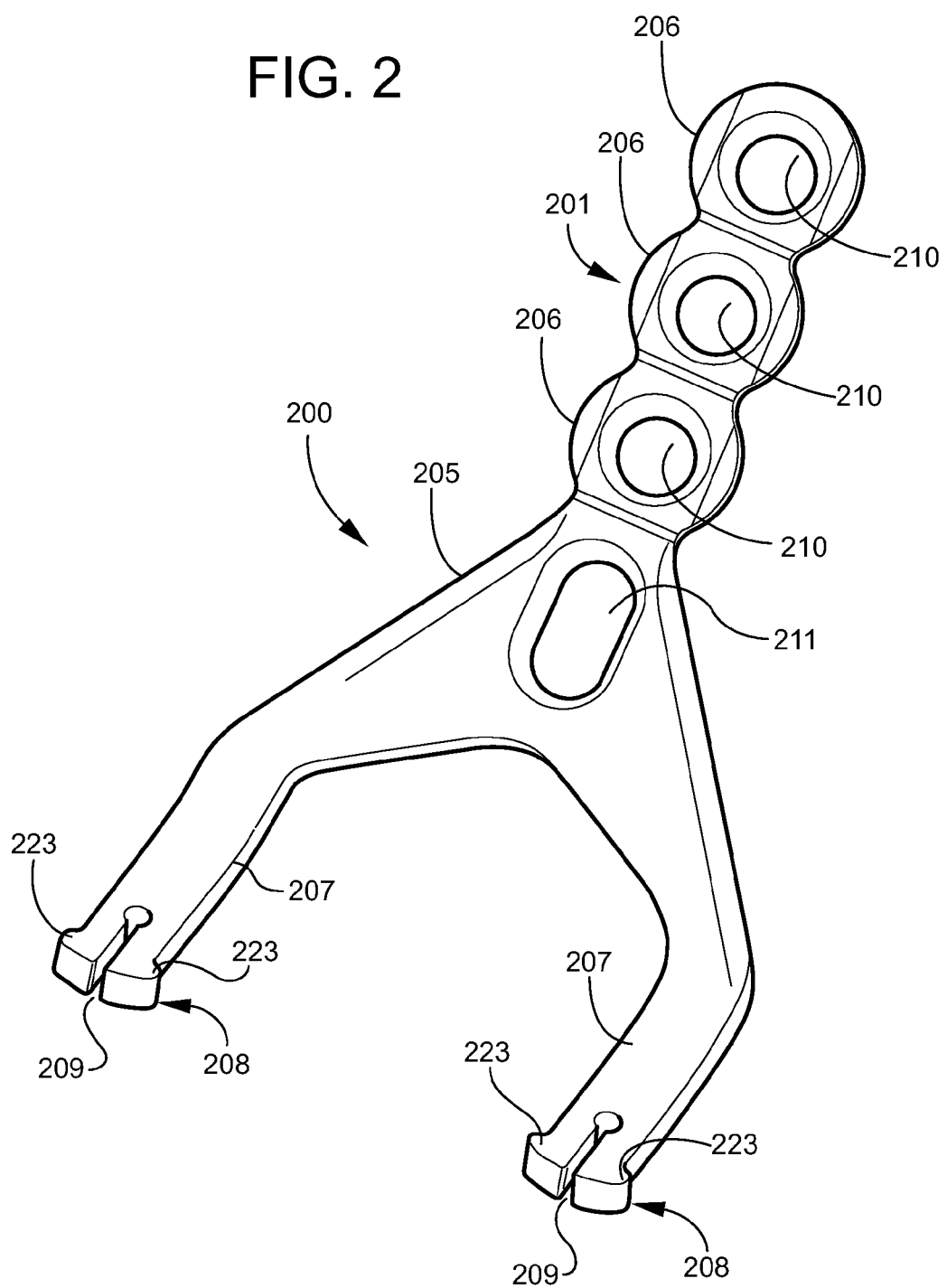
FIG. 2 illustrates a schematic diagram of an occipital plate according to an embodiment herein.

As shown in FIG. 2, the plate 200 comprises a generally centrally located base 205, a retaining end 201 extending from an upper portion of the base 205, and a pair of legs 207 substantially parallel (although other configurations are possible) to one another and extending from a bottom portion of the base 205, wherein the legs 207 extend at an angle substantially transverse to the axis of the base 205 and the retaining end 201. The plate 200 further includes caudal clips 223 at the end 208 of the legs 207. The clips 223 include a gap 209 to facilitate a bendable spring-like action of the clips 223 when squeezed together.

Moreover, the bendable occipital plate 200 is pre-angled to meet the average anatomy of the atlantoaxial joint. Furthermore, the plate 200 may be embodied as a one-piece Y-shaped component or two pre-curved assembled components that may be used for bilateral fixation. Also, the plate 200 can be cut to length if desired to avoid protrusion above the inion. Additionally, both legs 207 of the occipital plate 200 are placed on opposing cross-connectors 100 (of FIG. 1), which each attach to a longitudinal member 7 (of FIG. 1) of the spinal fusion construct (not shown). Also, the plate 200 is secured to the bone (not shown) of the occipital plateau with plate screws (not shown) through holes 210 of the retainer end 201. The holes 210 are preferably equally spaced in the retainer end 201 and are preferably centered in hole basins 206. Hole 211 is a slot for additional screw placement. Sometimes it is difficult to get screws in the caudal part of the occiput due to the inward curvature above the atlantoaxial joint. Some surgeons leave this area unfixed, while others try to get in as many screws a possible. Rather than having a fully constrained hole feature, the hole 211 is included for forgiveness in screw placement. In addition, holes 210 may be replaced with slots 211 in alternate embodiments. Additionally, both legs 207 of the plate 200 are adjustable for optimum placement.

As shown in FIG. 3, each cross-connector 100 comprises a flexible clip 9 having a concave portion 18 adapted to receive the longitudinal member 7 (of FIG. 1). The cross-connector 100 further comprises a connector body 2 having an inner socket 10 to receive the bulbous end 20 of a polyaxial connector head 3, which includes a slot 23 adapted to retain the caudal clips 208 of the end 220 of the legs 207 of the bendable Y-shaped or curved plate occipital plate 200 (of FIG. 2). Moreover, the clips 223 are configured to facilitate locking of the plate 200 once inserted into the slot 23 of the connector head 3. In addition, the connector head 3 is adjustable for optimum placement. Furthermore, each connector head 3 is locked by its internal preloaded set screw 6 such that the set screw 6 locks the connector head 3 in position to the legs 207 of the occipital plate 200, which then engages the locking pin 5, 105, 305 to lock the bulbous end 20 of the connector head 3 to the connector body 2, which causes the flexible clip 9 to lock onto the longitudinal member 7 all in one step.

In an alternative embodiment, the geometry of the connector body 2 may be modified for angle of placement on the longitudinal member 7. Furthermore, the socket 10 of the connector body 2 may be configured at various locations to provide varied offsets or heights of initial position. Additionally, the bendable occipital plate 200 may be a one-piece construct with the connector head 3. Also, the bendable occipital plate 200 may have a loose or tight fit with the connector head 3. The materials for all components of the assembly 1 may be various grades of metal, polymers, or shape-memory materials. For example, titanium grade materials, stainless steel materials, nitinol grades, ceramics, polyethylene, etc. may be used as the materials for constructing the assembly 1.

FIG. 4, with reference to FIGS. 1-3 and 5(A)-8(D), is a flow diagram illustrating a method of locking a longitudinal member 7 to a multi-pronged occipital plate 200 according to an embodiment herein, wherein the method comprises positioning (401) a longitudinal member 7 adjacent to a flexible clip 2; setting (403) a polyaxial connector head 3 in the flexible clip 2; inserting (405) a pin 5, 105, 305 in the polyaxial connector head 3, wherein the pin 5, 105, 305 contacts the flexible clip 2; inserting (407) a prong 207 of the occipital plate 200 in the polyaxial connector head 3; and attaching (409) a locking mechanism 6 to the polyaxial connector head 3, wherein the locking mechanism 6 is operatively connected to the pin 5, 105, 305. Preferably, attachment of the locking mechanism 6 to the polyaxial connector head 3 causes the prong 207 of the occipital plate 200 to engage the pin 5, 105, 305 thereby engaging the flexible clip 2 thereby causing the flexible clip 2 to lock the longitudinal member 7 into a locked position. Additionally, in the positioning process (401), the flexible clip 2 preferably comprises a flexible bias member 12, and wherein the flexible-bias member 12 is adapted to lock the longitudinal member 7 into a locked position. Furthermore, in the setting process (403), the polyaxial connector head 3 may comprise an upper portion 19 connected to a bulbous end 20, which is expandable and may be either symmetrical or non-symmetrical, wherein the upper portion 19 comprises a first hole 22 adapted to engage the locking mechanism 6; and a second hole 23 adapted to accommodate the occipital plate 200, wherein the first hole 22 and the second hole 23 are transversely positioned with respect to one another, wherein the bulbous end 20 comprises a plurality of flexible prongs 24 separated from one another by slots 25; and an opening 26 extending through the bulbous end 20 and extending to the first hole 22, wherein the pin 5, 105, 305 is adapted to engage the plurality of flexible prongs 24 causing the plurality of flexible prongs 24 to outwardly bend and lock the polyaxial connector head 3 to the flexible clip 2.

FIGS. 5(A) through 5(E) illustrate several views of the connector body 2 according to an embodiment herein. The connector body 2 is generally embodied as a one-piece construct (although multiple pieces fixed to one another are possible) and comprises a socket portion 8 attached to a longitudinal member receiving clip 9. The socket portion 8 comprises a generally hollowed inner socket 10 defined by an inner socket wall 15, an inner socket base 16, and an upper lip 13. An outer socket wall 14 provides the outer definition of the socket portion 8 of the connector body 2. The receiving clip 9 comprises a curved upper surface 11 having a concave portion 18 positioned on the underside of the curved upper surface 11. The concave portion 18 is dimensioned and configured to receive the longitudinal member 7 (of FIG. 1).

Figure 5B:
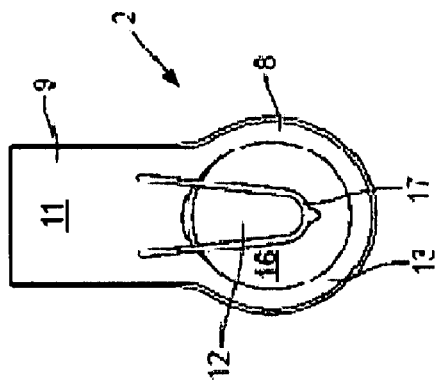
FIG. 5(B) illustrates a top view of the connector body of FIG. 5(A) according to an embodiment herein.

With reference to FIG. 5(B), which illustrates a top view of the connector body 2, the inner socket base 16 of the socket portion 8 is generally circular in shape and it is on this base 16 where the connector head 3 and locking pin 5, 105, 305 (of FIG. 3) rest. The inner socket base 16 further includes a gap 17, which creates a separation between the inner socket base 16 and a bias member 12 of the connector body 2. The bias member 12 may be configured as a spring, flange, or flexible structure. The gap 17 extends up to and in the receiving clip 9, and when viewed from the top (as in FIG. 5(B)) the gap 17 may appear to be V-shaped although other shapes are possible, and the embodiments herein are not limited to any particular shape or geometry. Generally, the bias member 12 is an extension of the receiving clip 9 as it is retained in a cantilever manner to the connector body 2 only by the receiving clip 9 and does not contact the socket portion 8 due to the gap 17. Preferably, the thickness of the gap 17 is uniform, but may include a slightly larger gap area towards the bottom of the gap 17 (i.e., bottom of the V-shape).

Figure 5A:
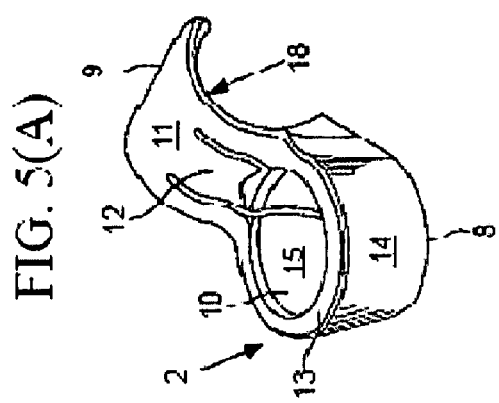
FIG. 5(A) illustrates a perspective view of the connector body of the spinal cross-connector assembly construct of FIG. 3 according to an embodiment herein.
Figure 5E:
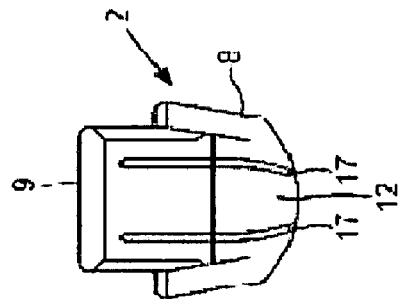
FIG. 5(E) illustrates a back view of the connector body of FIG. 5(A) cut along line B-B of FIG. 5(D) according to an embodiment herein.
Figure 5D:
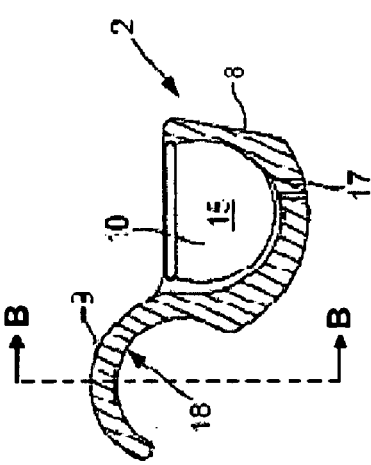
FIG. 5(D) illustrates a cross-sectional side view of the connector body of FIG. 5(A) cut along line A-A of FIG. 5(C) according to an embodiment herein.
Figure 5C:
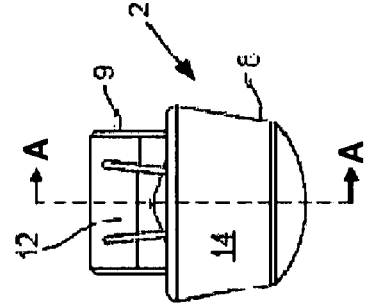
FIG. 5(C) illustrates a front view of the connector body of FIG. 5(A) according to an embodiment herein.

FIG. 5(D) illustrates a cross-sectional side view of the connector body 2 of FIG. 5(A) taken along line A-A of FIG. 5(C). In this view, the relative thicknesses of the socket portion 8 and receiving clip 9 can be seen as well as the relative depth of the gap 17. Additionally, the configuration of the concave portion 18 of the receiving clip 9 can be seen as generally matching the cylindrical configuration of the longitudinal member 7 (of FIG. 1). FIG. 5(E) illustrates a back view of the connector body 2 of FIG. 5(A) taken along line B-B of FIG. 5(D), and further illustrates the general configuration of the gap 17.

FIGS. 6(A) through 6(E) illustrate several views of the connector head 3 of the spinal cross-connector assembly 1 of FIG. 1 according to an embodiment herein. Preferably, the connector head 3 is a one-piece construct (although multiple pieces fixed to one another are possible) and comprises an upper portion 19 connected to a lower bulbous end 20. The upper portion 19 is defined by a generally curved outer wall 21 having an upper cavity hole 22 and a leg receiving hole 23 configured therein. Preferably, the upper cavity hole 22 is positioned along a longitudinal axis of the connector head 3 and the leg receiving hole 23 is positioned along an axis transverse to the longitudinal axis of the connector head 3, and thus the upper cavity hole 22 is preferably transverse to the leg receiving hole 23. The leg receiving hole 23 extends through the outer wall 21 of the connector head 3 and the upper cavity hole 22 extends longitudinally through the connector head 3 and terminates with an opening 26 at the bottom of the bulbous end 20 of the connector head 3. Threads 28 are configured in the upper portion 19 of the connector head 3 and are dimensioned and configured to receive the set screw 6 (of FIG. 3).

An inner connector base 27 generally separates the upper portion 19 of the connector head 3 from the bulbous end 20 of the connector head 3, wherein the inner connector base 27 is preferably flat to facilitate an even positioning of the legs 207 of the plate 200 (of FIG. 2). Moreover, the bulbous end 20 preferably comprises a generally spherical configuration having a plurality of downward-turned prongs 24 spaced apart from one another by slots 25. The prongs 24 are flexible to allow expansion of the bulbous end 20 of the connector head 3 into the inner socket 10 of the connector body 2. Additionally, a pin cavity 29 is configured in the bulbous end 20 of the connector head 3 to accommodate the locking pin 5, 105, 305 (of FIG. 3), wherein the upper part of the pin cavity 29 begins at the position of the inner connector base 27, and the lower part of the pin cavity 29 terminates at the opening 26 in the bulbous end 20 of the connector head 3.

FIG. 6(B) illustrates a cross-sectional top view of the connector head 3 of FIG. 6(A) taken along line D-D of FIG. 6(C). In this view, the relative thickness of the upper portion 19 of the connector head 3 is illustrated. FIG. 6(D) illustrates a cross-sectional front view of the connector head 3 of FIG. 6(A) taken along line C-C of FIG. 6(C), and FIG. 6(E) illustrates a cross-sectional side view of the connector head 3 of FIG. 6(A) cut along line E-E of FIG. 6(D). In these views, the threads 28 and pin cavity 29 can best be seen.

Figure 7A:
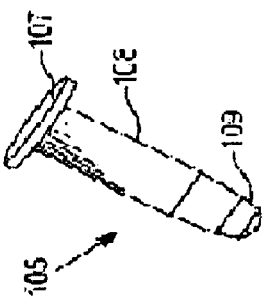
FIG. 7(A) illustrates a perspective view of the locking pin of the spinal cross-connector assembly construct of FIG. 3 according to an embodiment herein.

FIG. 7(A) illustrates a perspective view of the locking pin 105 (of FIG. 3), which comprises a generally planar upper portion 107 and a stem portion 108 extending from the upper portion 107. The stem portion 108 ends with a generally tapered section 109. The locking pin 105 is configured to fit into the pin cavity 29, which is configured in the bulbous end 20 of the connector head 3 (of FIGS. 6(D) and 6(E)).

Figure 7D:
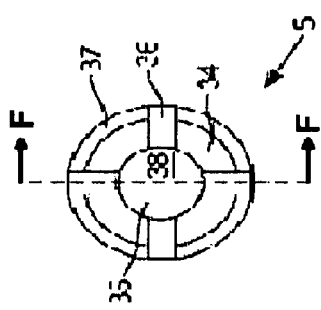
FIG. 7(D) illustrates a top view of the locking pin of FIG. 7(A) according to a first alternate embodiment herein.
Figure 7E:
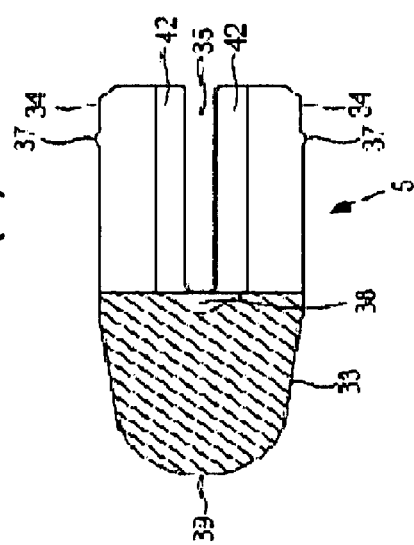
FIG. 7(E) illustrates a cross-sectional side view of the locking pin of FIG. 7(B) cut along line F-F of FIG. 7(D) according to a first alternate embodiment herein.
Figure 7C:
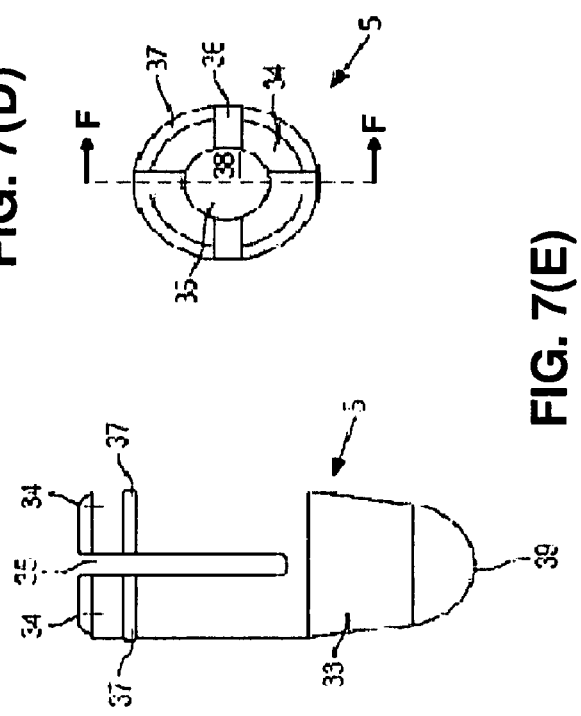
FIG. 7(C) illustrates a side view of the locking pin of FIG. 7(A) according to a first alternate embodiment herein.
Figure 7B:
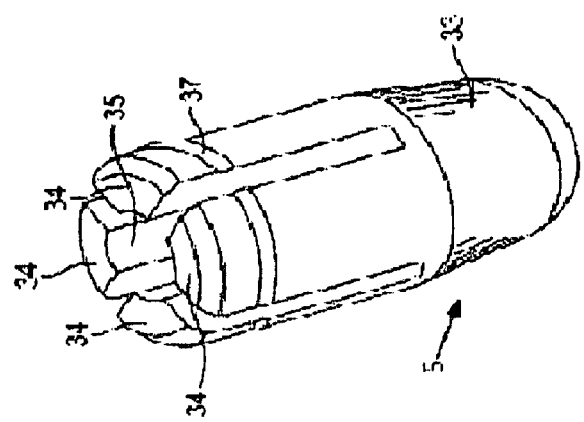
FIG. 7(B) illustrates a perspective view of the locking pin of the spinal cross-connector assembly construct of FIG. 3 according to a first alternate embodiment herein.

FIGS. 7(B) through 7(E) illustrate several views of another locking pin 5, which may be used in the connector 100 (of FIG. 3) according to a first alternate embodiment herein. The locking pin 5 is preferably embodied as a one-piece construct (although multiple pieces fixed to one another are possible). The locking pin 5 comprises a lower end 33 terminating with a tip 39. Extending from the lower end 33 and distally away from the tip 39 is a plurality of upper members 34 separated from one another by slots 36. Preferably, the shape of the upper members 34 follows the contour of the shape of the lower end 33 of the locking pin 5, wherein the overall contour of the locking pin 5 is dimensioned and configured to fit into the pin cavity 29 of the connector head 3 (of FIGS. 6(D) and 6(E)). A central hole 35 is configured in the locking pin 5 and in between the plurality of upper members 34 such that the combination of the central hole 35 and slots 36 create pronglike upper members 34. The central hole 35 terminates with a central hole base 38, which acts as a positional separation between the lower end 33 of the locking pin 5 and the upper members 34 of the locking pin 5. Additionally a lip 37 is configured on each of the upper members 34, wherein the lips 37 of all of the upper members 34 are aligned to one another to form a substantially circular shape when viewed from the top as illustrated in FIG. 7(D). The lips 37 of the upper members 34 are adapted to lock the locking pin 5 into connector head 3 (of FIGS. 6(A) through 6(E)) to prevent backout of the connector head 3 from the connector body 2 (of FIGS. 5(A) through 5(E)). Lips 37 fit into the undercut diameter slot 44 of the connector head shown 3 in FIG. 6(D). FIG. 7(E) illustrates a cross-sectional side view of the locking pin 5 of FIG. 8(A) taken along line F-F of FIG. 7(D). In this view, the edges 42 of the upper members 34 can be seen as well as the preferred conical shape (although other shapes are possible) of the central hole base 38.

FIGS. 7(F) through 7(I) illustrate several views of yet another locking pin 305 of the spinal cross-connector assembly construct 100 (of FIG. 3) according to a second alternate embodiment herein. The locking pin 305 is preferably embodied as a one-piece construct (although multiple pieces fixed to one another are possible). The locking pin 305 comprises an upper end 337 that is connected to a sloping middle portion 338 that is connected to lower end 333 terminating with a substantially flat end 339. The upper end 337 has an interrupted cylindrically longitudinal shape having a curved outer wall 334. One side of the curved outer wall 334 comprises a protruding portion 335 extending therefrom, wherein the protruding portion 335 comprises an angled ramp 391 configured therein. The angled ramp 391 is configured to create a ramp for smooth interaction with the connector body 2 (of FIGS. 5(A) through 5(E)) in a manner described in the '380 cross-connector patent application. The configuration of the upper end 337 provides increased locking in one direction (direction where the protruding portion 335 is). Additionally, the lower end 333 comprises a unidirectional lip 336 extending from a side of the lower end 333. The lip 336 allows for permanent assembly of the locking pin 305 in the inner socket 10 of the connector body 2 (of FIGS. 5(A) through 5(E)). The lower end 333 and lip 336 are adapted to engage the flexible bias member 12 of the connector body 2 (of FIGS. 5(A) through 5(E)) causing the longitudinal member 7 (of FIG. 1) to become locked by the receiving clip 9 of the connector body 2 (of FIGS. 3 and 5(A) through 5(E)).

Preferably, the overall contour of the locking pin 305 is dimensioned and configured to fit into the pin cavity 29 of the connector head 3 (of FIGS. 6(D) and 6(E)). FIG. 7(I) illustrates a cross-sectional side view of the locking pin 305 of FIG. 7(H) cut along line G-G of FIG. 7(H). In this view, the contour of the lip 336 with respect to the upper end 337 can be seen (although other contours and shapes are possible so long as they match the corresponding configuration of the pin cavity 29 of the connector head 3 (of FIGS. 6(D) and 6(E)).

Figure 8B:
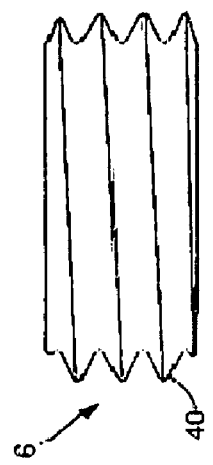
FIG. 8(B) illustrates a side view of the set screw of FIG. 8(A) according to an embodiment herein.
Figure 8D:
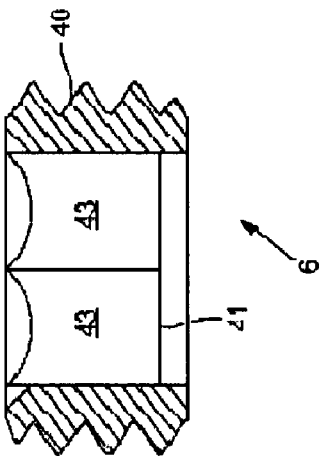
FIG. 8(D) illustrates a cross-sectional side view of the set screw of FIG. 8(A) cut along line H-H of FIG. 8(C) according to an embodiment herein.
Figure 8A:
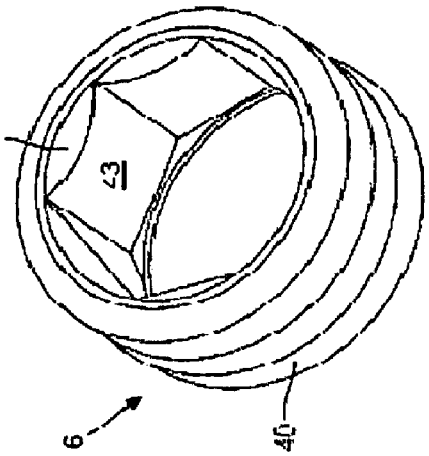
FIG. 8(A) illustrates a perspective view of the set screw of the spinal cross-connector assembly construct of FIG. 3 according to an embodiment herein.
Figure 8C:
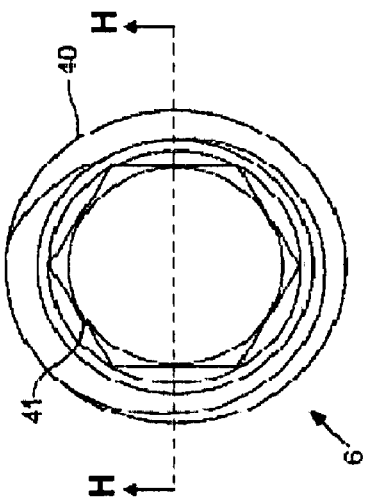
FIG. 8(C) illustrates a top view of the set screw of FIG. 8(A) according to an embodiment herein.

FIGS. 8(A) through 8(D) illustrate several views of the set screw 6 of the spinal cross-connector assembly 1 of FIG. 1 according to an embodiment herein. Generally, the set screw 6 may be any type of blocker used to retain the transverse member 4 and locking pin 5, 105, 305 in place in the connector head 3 (of FIGS. 3 and 6(A) through 6(E)). In one embodiment, the set screw 6 comprises threads 40 positioned around an outer periphery of the set screw 6 and dimensioned and configured to engage the threads 28 of the connector head 3 (of FIGS. 6(D) and 6(E)). Moreover, the set screw 6 comprises a fastening feature 41, which may be configured to accommodate a screwdriver (hex, torx, flat-head, Phillips, etc.) or similar mechanism. Alternatively, if the threads 28 of the connector head 3 (of FIGS. 6(D) and 6(E)) are configured along the outer wall 21 of the connector head 3, then the corresponding threads 40 of the set screw 6 are configured along the inner wall 43 of the set screw 6 of FIG. 8(A). FIG. 8(D) illustrates a cross-sectional side view of the set screw 6 of FIG. 8(A) cut along line H-H of FIG. 8(C), which further shows the inner wall 43 of the set screw 6.

The assembly 1 generally provides rotation by a polyaxial connector 100 mechanism with an occipital plate member 200 that can be bent and translated within the connector polyaxial head 3 for greater ease of placement. Moreover, the assembly 1 provides a user-friendly top loading connection with a one-step locking mechanism while providing six-degrees of freedom for easier placement over the atlantoaxial joint. The six-degrees of freedom that are achieved are: (1) connector body 2 slides on longitudinal member 7; (2) connector body 2 rotates on longitudinal member 7; (3) connector head 3 rotates sagittal in connector body 2; (4) connector head 3 rotates transverse in connector body 2; (5) connector head 3 rotates coronal in connector body 2; and (6) occipital plate 200 slides in connector head 3 (the occipital plate 200 can also slightly rotate transverse in the connector head 3 due to tolerance gap).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A polyaxial occipital plate assembly that engages a longitudinal member, said assembly comprising:
    a polyaxial connector head;
    a socket portion adapted to retain said polyaxial connector head;
    a flexible clip operatively connected to said socket portion and adapted to receive said longitudinal member, wherein said flexible clip comprises a flexible bias member adapted to retain said longitudinal member;
    an occipital plate comprising clips operatively connected to said polyaxial connector head, wherein said occipital plate comprises:
        a body portion;
        a first leg extending from said body portion; and
        a second leg extending from said body portion,
        wherein the first and second legs are substantially parallel to one another,
            wherein the first and second legs each comprise slotted caudal ends that are adapted to fit through said polyaxial connector head; and
    a locking mechanism operatively connected to said polyaxial connector head and said clips, wherein said locking mechanism comprises a pin portion operatively connected to said socket portion and said polyaxial connector head, wherein engagement of said locking mechanism to said polyaxial connector head causes said clips to lock into said polyaxial connector head and causes said slotted caudal ends to push said pin portion thereby causing outward expansion of said polyaxial connector head thereby causing said flexible bias member to squeeze against said longitudinal member.

2. The assembly of claim 1, wherein said occipital plate further comprises:
    wherein said body portion is positioned at any of an obtuse angle and an acute angle relative to said first and second legs.

3. The assembly of claim 1, wherein said flexible bias member is separated from said socket portion by a gap.

4. The assembly of claim 1, wherein said locking mechanism comprises:
    a blocker mechanism operatively connected to said clips and said polyaxial connector head,
    wherein said pin portion is adapted to engage said flexible bias member causing said longitudinal member to become affixed to said flexible clip.

5. The assembly of claim 1, wherein said polyaxial connector head comprises an upper portion comprising:
    a first hole that accommodates said locking mechanism; and
    a second hole that accommodates said clips of said occipital plate,
    wherein said first hole and said second hole are transversely positioned with respect to one another.

6. The assembly of claim 5, wherein said polyaxial connector head comprises a bulbous end connected to said upper portion, and wherein said bulbous end sits in said socket portion, said bulbous end comprising:
    a plurality of flexible prongs separated from one another by slots; and
    an opening extending through said bulbous end and extending to said first hole.

7. The assembly of claim 6, wherein said locking mechanism engages said plurality of flexible prongs causing said plurality of flexible prongs to outwardly bend and lock said polyaxial connector head to said socket portion.

8. The assembly of claim 1, wherein each of said clips of said occipital plate are bendable.

9. An occipital plate assembly comprising:
a longitudinal member;
a connector body comprising a flexible bias member adapted to retain said longitudinal member;
a connector head adapted to engage said connector body;
a pin operatively connected to said connector body and said connector head;
an occipital plate operatively connected to said connector head and said pin; and
a blocker operatively connected to said connector head and contacting said occipital plate;
wherein said occipital plate comprises:
a body portion;
a first leg extending from said body portion; and
a second leg extending from said body portion,
wherein the first and second legs are substantially parallel to one another,
wherein the first and second legs each comprise slotted caudal ends that are adapted to fit through said connector head, and
wherein engagement of said blocker to said connector head causes said slotted caudal ends to push said pin thereby causing outward expansion of said connector head thereby causing said flexible bias member to lock said longitudinal member to said connector body.

10. The assembly of claim 9, wherein said connector body comprises:
a socket portion; and
a clip portion attached to said socket portion, said clip portion being adapted to retain said longitudinal member,
wherein said flexible bias member extends from said clip portion to a bottom region of said portion.

11. The assembly of claim 9, wherein said pin is adapted to engage said flexible bias member causing said longitudinal member to become locked to said connector body.

12. The assembly of claim 9, wherein said connector head comprises an upper portion comprising:
a first opening adapted to engage said locking mechanism; and
a second opening adapted to accommodate said occipital plate,
wherein said first opening and said second opening are transversely positioned with respect to one another.

13. The assembly of claim 12, wherein said connector head comprises a bulbous end comprising:
a plurality of flexible prongs separated from one another by slots; and
a hole extending through said bulbous end and extending to said first opening.

14. The assembly of claim 13, wherein said pin is adapted to engage said plurality of flexible prongs causing said plurality of flexible prongs to outwardly bend and lock said bulbous end of said connector head to said flexible clip.

15. A method of locking a longitudinal member to a multi-pronged occipital plate, said method comprising:
positioning a longitudinal member adjacent to a connector body, wherein said connector body comprises a flexible bias member adapted to retain said longitudinal member;
engaging a connector head to said connector body;
inserting a pin in said connector head, wherein said pin contacts said connector body;
inserting said occipital plate in said connector head, wherein said occipital plate contacts said pin; and
engaging a blocker to said connector head, wherein said blocker contacts said occipital plate, wherein said occipital plate comprises:
a body portion;
a first leg extending from said body portion; and
a second leg extending from said body portion,
wherein the first and second legs are substantially parallel to one another,
wherein the first and second legs each comprise slotted caudal ends that are adapted to fit through said connector head, and
wherein engagement of said blocker to said connector head causes said slotted caudal ends to push said pin thereby causing outward expansion of said connector head thereby causing said flexible bias member to lock said longitudinal member to said connector body.

16. The method of claim 15, wherein said connector body comprises:
a socket portion; and
a clip portion attached to said socket portion, said clip portion being adapted to retain said longitudinal member,
wherein said flexible bias member extends from said clip portion to a bottom region of said portion.

17. The method of claim 15, wherein said pin is adapted to engage said flexible bias member causing said longitudinal member to become locked to said connector body.

18. The method of claim 15, wherein said connector head comprises an upper portion comprising:
a first opening adapted to engage said locking mechanism; and
a second opening adapted to accommodate said occipital plate,
wherein said first opening and said second opening are transversely positioned with respect to one another.

19. The method of claim 18, wherein said connector head comprises a bulbous end comprising:
a plurality of flexible prongs separated from one another by slots; and
a hole extending through said bulbous end and extending to said first opening.

20. The method of claim 19, wherein said pin is adapted to engage said plurality of flexible prongs causing said plurality of flexible prongs to outwardly bend and lock said bulbous end of said connector head to said flexible clip.

* * * * *